United States Patent [19]

Chen

[11] Patent Number: 4,957,836

[45] Date of Patent: Sep. 18, 1990

[54] ELECTROPHOTORECEPTOR USING HYDRAZONE AS THE CHARGE TRANSPORT MATERIAL

[75] Inventor: Tai J. Chen, Hsinchu, Taiwan

[73] Assignee: Industrial Technology Research Institute, Chutung, Hsinchu, Taiwan

[21] Appl. No.: 357,370

[22] Filed: May 25, 1989

[51] Int. Cl.⁵ .............................................. G03G 5/14
[52] U.S. Cl. ..................................................... 430/59
[58] Field of Search ......................................... 430/59

[56] References Cited

U.S. PATENT DOCUMENTS

| | | | |
|---|---|---|---|
| 4,278,747 | 7/1981 | Murayama et al. | 430/59 X |
| 4,786,571 | 11/1988 | Ueda | 430/59 |
| 4,830,944 | 5/1989 | Umehara et al. | 430/59 |

Primary Examiner—J. David Welsh
Attorney, Agent, or Firm—Scully, Scott, Murphy & Presser

[57] ABSTRACT

An electrophotoreceptor comprising a conductive substrate, a charge generation layer and a charge transport layer wherein the charge transport layer comprises a polymeric binder and a hydrazone compound as the charge transport material. The photoreceptor exhibits improved sensitivity, residual potential, durability and reproductibility.

13 Claims, No Drawings

ELECTROPHOTORECEPTOR USING HYDRAZONE AS THE CHARGE TRANSPORT MATERIAL

BACKGROUND OF THE INVENTION

Since the invention of xerography (which means "dry writing" in Greek) by C Carlson in 1938, new facilities utilizing this technique such as xerox copier, laser printer and optical printer have provided inexpensive, convenient and fast services of copying documents and played important roles in office automation.

The focus of the xerographic technique resides in the electrophotoreceptor which is an optical element electrically insulative in darkness and becomes electrically conductive after exposure under light The xerographic process comprises mainly five steps, namely, (1) charging, (2) photodischarging, (3) image transfer, (4) development and (5) cleaning In order to obtain printed images high quality, the photoreceptor must have high charge acceptance, low dark conductivity and fast photoconductvity (i.e., high sensitivity).

Photoreceptors can be classified as inorganic or organic. Typical inorganic charge generation materials include, for example, selenium, cadmium sulfide, zinc oxide and amorphous silicon. On the other hand, there are numerous organic charge generation materials, examples for which are photoconductive polymers such as poly-N-vinylcarbazole and polyvinylanthrancene, low molecular weight organic compounds such as carbazole, anthracene, oxadiazole, certain hydrazones and certain polyarylalkanes, organic pigments or dyes such a phthalocyanine pigment, azo pigment, cyanine pigment, polycyclic quinone pigment, perylene pigment, indigo dye, thioindigo dye and squaraine dye. Due to their advantages in low production cost, non-toxicity and high flexibility in utilization, organic photoreceptors (OPC) have replaced inorganic photoreceptors as the predominant photoreceptors among the commercialized photoreceptors.

The structures of photoreceptors may be classified as (1) mono layer type, such as that disclosed in n U.S. Pat. No. 3,484,237, (2) functionally separated laminated type, such as those described in U.S. Pat. Nos. 3,837,851, 3,850,630, 4,123,270 and 4,293,628, and (3) microcrystalline distribution type. The functionally separated laminated layer type is the most preferred because it contains separated charge generation layer (CGL) and charge transport layer (CTL) and thus is highly flexible in the selection of materials for each layer. The characteristics and requirements may be adjusted independently in CGL or CTL. This type of photoreceptors are predominant among the present photoreceptors.

The functionally separated laminated type photoreceptors are generally composed of a conductive substrate, a charge generation layer and a charge transport layer. An optional barrier layer or an adhesive layer may be inserted between the conductive substrate and the charge generation layer. In the production of photoreceptors of this type, a charge generation layer composed of a charge generation material and a polymeric binder is coated on a conductive support and then a charge transport layer composed of a charge transport material and another polymeric binder is coated.

Organic charge transport materials have the advantages in multiplicity of selection and ease of synthesis. Extensive research therefore has been dedicated in this respect and organic charge transport materials have been becoming more important among present charge transport materials.

Organic photoreceptor may be produced by selecting suitable charge generation material, charge transport material and polymeric binders. A simple process with high productivity can be employed. However, conventional organic photoreceptors suffer from some disadvantages such as low sensitivity high residual surface potential and bad reproducibility after repeated uses. The improvement of the these properties have always been sought after.

SUMMARY OF THE INVENTION

Accordingly, it is thus an object of the present invention to provide an organic photoreceptor with high sensitivity, low residual surface potential, good durability and reproducibility (that the residual potential will not accumulate after repeated use).

The subject invention in its broadest context encompasses an electrophotoreceptor comprising the components of:

an electrically conductive substrate;

a charge generation layer on top of said substrate comprising a charge generation material capable of generating electron-hole pair upon exposure under a selected light ;and a charge transport layer comprising a polymeric binder and a hydrazone compound of formula (I)

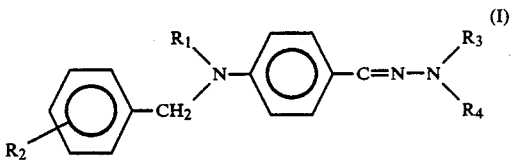

in which $R_1$ represents substituted or unsubstituted $C_1$–$C_4$ alkyl, $R_2$ represents hydrogen, alkyl or alkoxy, $R_3$ and $R_4$ independently represent substituted or unsubstituted alkyl group, substituted or unsubstituted aryl group or substituted or unsubstituted aralkyl group, or together with the bonded nitrogen atom represent substituted Or unsubstituted aromatic heterocyclic ring.

DETAILED DESCRIPTION OF THE INVENTION

It was unexpectedly found that high sensitivity, low residual potential and excellent durability can be realized on a electrophotoreceptor by employing a specific group of hydrazone compounds as the charge transport material.

The individual elements of the present invention are described in detail below.

The hydrazone compounds contemplated by the present invention are compounds of formula (I):

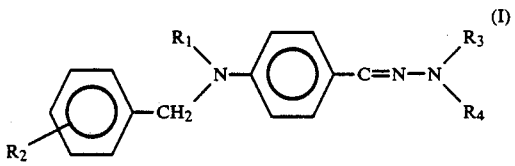

in which $R^1$ represents substituted or unsubstituted $C_1$–$C_4$ alkyl, $R_2$ represents hydrogen, alkyl or alkoxy, $R_3$ and $R_4$ independently represent substituted or unsubstituted alkyl group, substituted or unsubstituted aryl group or substituted or unsubstituted aralkyl group, or together with the bonded nitrogen atom represent substituted or unsubstituted aromatic heterocyclic ring.

A preferred group of hydrazone compounds contemplated by the present invention are compounds of formula (I) in which at least one of $R_3$ and $R_4$ is an aryl group.

A more preferred group of hydrazone compounds contemplated by the present invention are compounds of formula (I) in which $R_1$ represents ethyl and $R_2$ represents hydrogen.

A group of most preferred hydrazone compound contemplated by the present invention are compounds as follows:

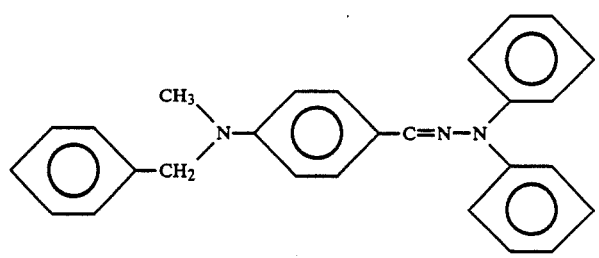

1

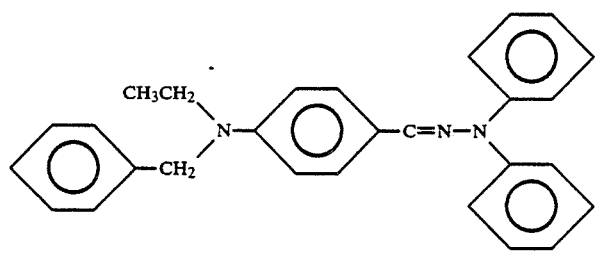

2

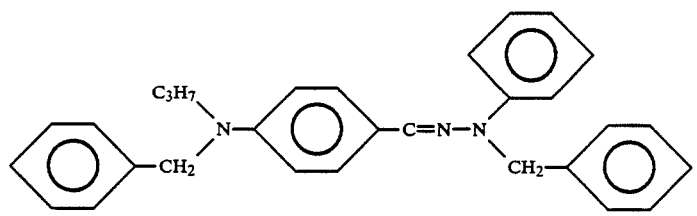

3

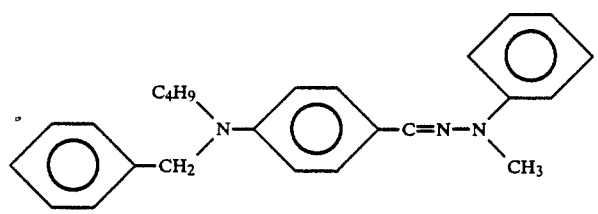

4

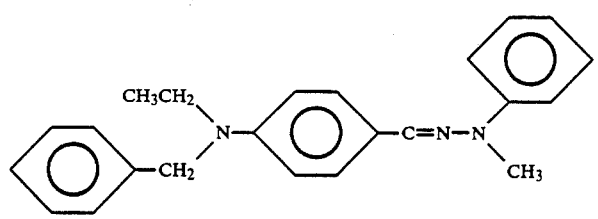

5

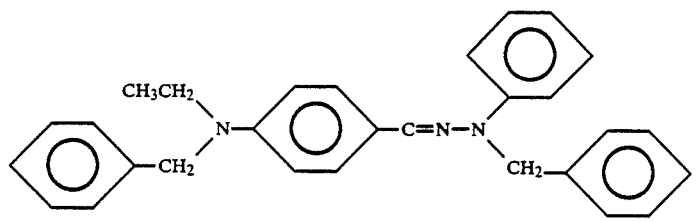

6

-continued
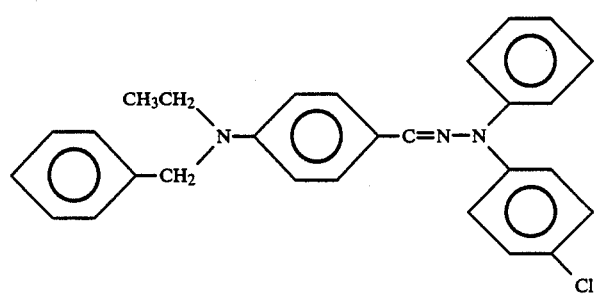
7
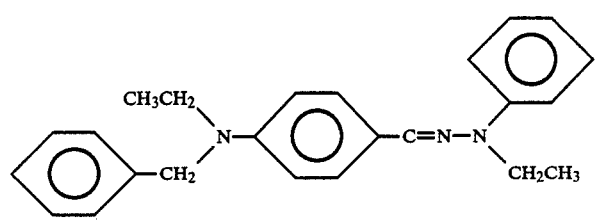
8
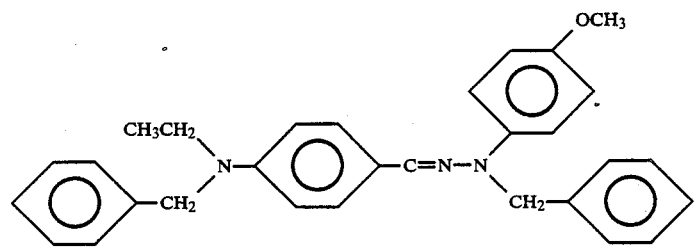
9
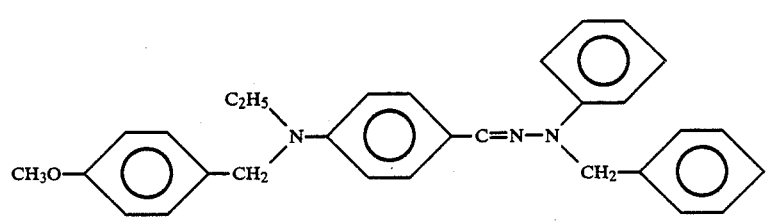
10
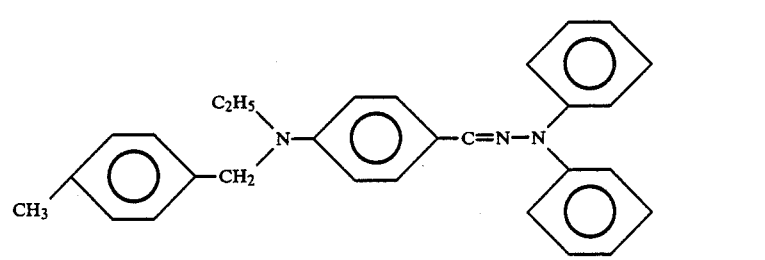
11
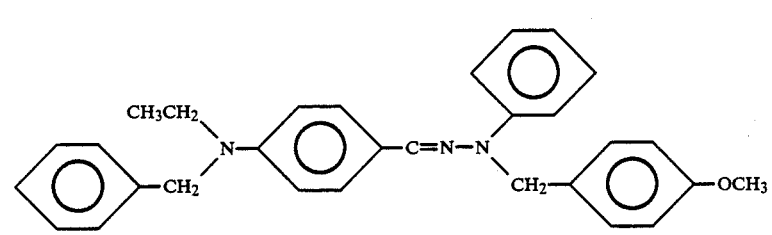
12

13
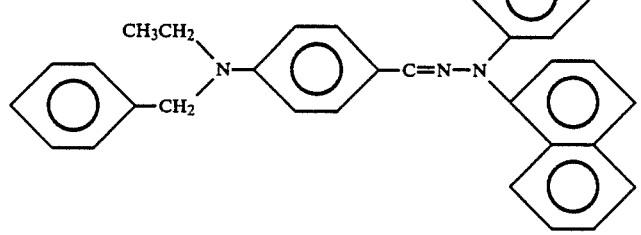
14
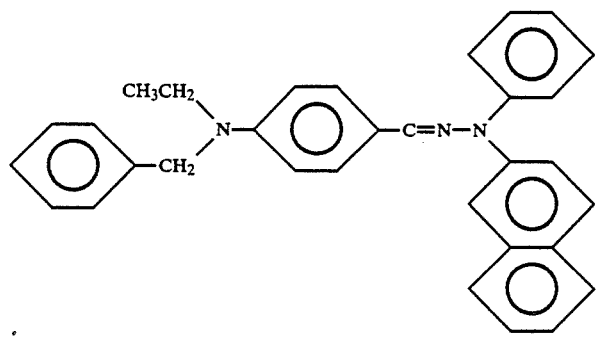
15
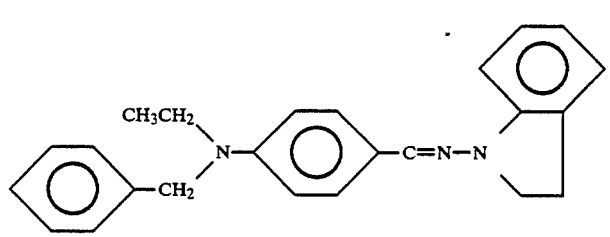
16
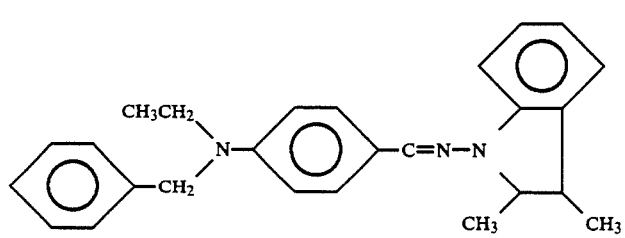
17
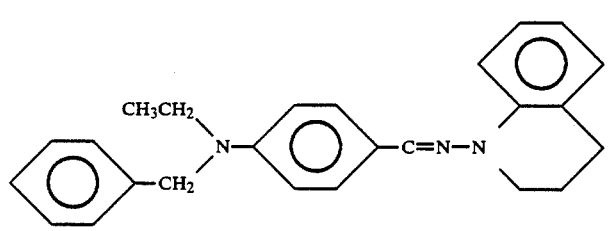
18
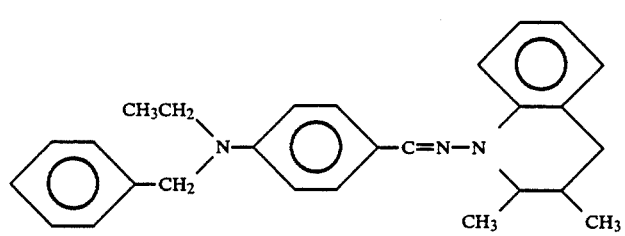

-continued

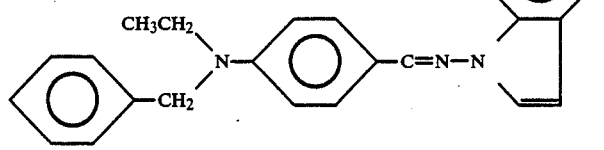 19

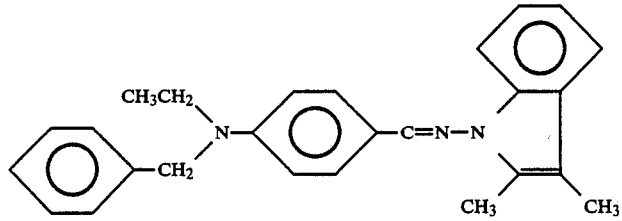 20

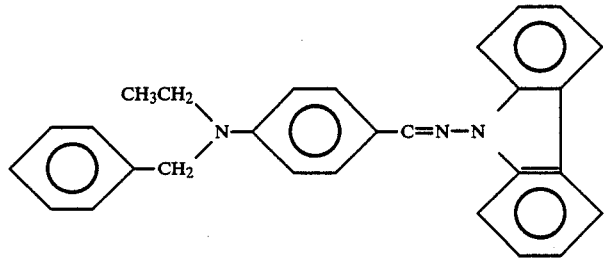 21

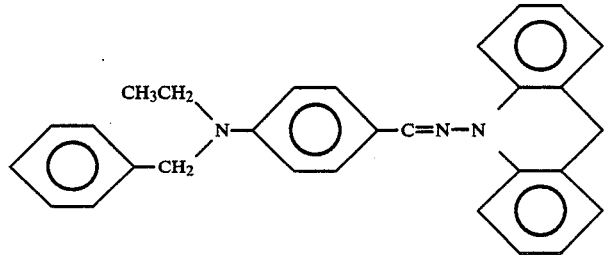 22

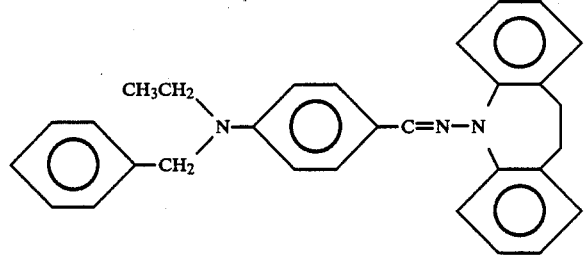 23

The hereinabove described hydrazone compounds can be produced by conventional methods. For example, the hydrazone compounds can be obtained by reacting equimolar aldehyde and hydrazine in a suitable solvent using an organic or inorganic acid as the catalyst. Hydrazine is frequently added in excess to ensure complete reaction and ease of purification. The solvents commonly employed include alcohol, acetic acid and tetrahydrofuran.

In the production of an electrophotoreceptor according to the present invention, the conductive substrate is coated with the described charge generation layer and then the charge transport layer. The charge generation layer is applied by coating on the conductive substrate a solution containing a charge generation material and a polymeric binder followed by drying said dispersion. A charge transport layer is then applied over the charge generation layer by coating a solution of the above described hydrazone in another polymeric binder and then drying the solution The coating can be effected by any conventional methods such as blade coating, dipping and spraying.

The dry film thickness of the charge generation layer is generally from 0.01 g/m² to 5 g/m², preferably from 0.04 g/m² to 2 g/m². The dry film thickness of the charge transport layer is generally from 3 to 50 um, preferably from 10 to 25 um. The content of the hydrazone compound in the charge transport layer is from 10 wt% to 95 wt%, preferably from 30 wt% to 80 wt%.

The charge generation materials that may be used in the charge generation layer of the present invention are, for example inorganic pigments such as selenium, selenium-tellurium alloy, selenium-arsenic alloy and cadmium sulfide, and organic pigments such as phthalocyanine pigment, perinone pigment, thioindigo pigment, quinacridone pigment, perylene pigment, anthraquine pigment, azo pigment, bisazo pigment, cyanine pigment and squaraine pigment.

Some compounds which may form a complex with the hydrazone compound can also be added in the charge transport layer to improve the photoconductivity of the charge transport material of the present invention. These complex forming compounds are, for example, quinones such as chloranil, 2,3-dichloro-1,4-naphthoquinone, 1-chloro-5-nitro anthraquinone, aldehydes such as 4-nitrobenzaldehyde, ketones such as indandione, 3,5-dinitrobenzophenone, 2,4,7-trinitrofluorenone anhydrides such as phthalic anhydride, 4-chlkoro-naphthalic anhydride, cyanide such as terephthalmalonitrile, phthalides such as benzal phthalide, 3-a-cyano-p-nitrobenzal phthalid.

The polymeric binders which can be used in combination with the hydrazone compounds of the present invention are, for example, vinyl polymers or copolymers of styrene, vinyl acetate, acrylates, polyvinyl acetates, polycarbonates, polyesters, polysulfones, polyphenylene oxides, polyurethanes, cellulose esters, etc.

In a further preferred embodiment, a adhesive layer may be introduced between the conductive substrate and the charge generation layer to prevent the reverse injection of electrons from the conductive support into the charge generation layer. Materials suitable for use as such adhesive are, for example, polyamides, polyvinyl alcohol, casein, nitro cellulose and methyl cellulose. The thickness of the adhesive layer is generally from 1 to 5 um.

If necessary, a plasticizer may be added in charge transport layer to improve its film forming ability. The plasticizers suitable for use in the present invention include, for example, phthalic acid ester, epoxy compounds, chlorinate paraffin, methyl-naphthalene.

The hydrazone compounds selected by the present invention possess high charge transport efficiency, can be used in association with various types of charge generation materials, and possess high compatibility with many resins. The charge transport layer made therefrom therefore has high durability and, most important of all, possesses high transparency which improves the transmission of incident light through the charge transport layer and renders complete absorption of incident light by the charge generation layer. With this outstanding property, the electrophotoreceptor made in accordance with the present invention is imparted with high sensitivity, low residual potential, and the sensitivity will not change and the residual potential will not accumulate even after repeated use.

The following examples are offered to aid in understanding of the present invention and are not to be construed as limiting the scope thereof.

EXAMPLES

Example 1

A binder mixture containing 10 g of a polyamide copolymer (CM8000 available from Toray Co., Japan), 60 g of methanol and 40 g of n-butanol is dip-coated on a aluminium plate of 0.2 mm thickness. The coating was then dried by heating in a hot air oven for 30 minutes. An adhesive layer of 1.0 g/m² thickness was obtained A charge generation layer coating containing 0.68 g of epsilon-type copper phthalocyanine (Heleigen Blue L0700 available from BASF), 0.068 of hydroxy squaraine (HOSq) of the formula

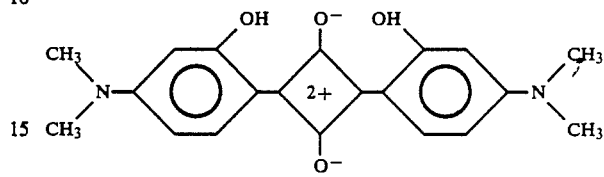

0.75 g polyvinyl butyral (BM2 available from Sekisui Co., Japan), 24.25 g of cyclohexanone and 24.25 g of bulanone was mixed by a mlcronizing mill product of McCrone, United Kingdom) for 6 hours. The resultant coating was then applied by dipping on the adhesive layer and dried by heating in a hot air oven at 80° C. for 30 minutes. A charge generation layer of 0.3 g/m² thickness was obtained.

A charge transport layer coating solution containing 0.5 g of a hydrazone compound of the formula:

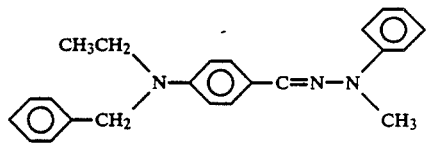

0.75 g of a styrene-maleic anhydride copolymer (Dylark 232 available from Arco Co., Japan), and 4 g of toluene as the solvent was coated on the charge generation layer and then dried by heating it in a hot oven of 100° C. for 60 minutes. A charge transport layer of 20 um was obtained.

The resultant organic photoreceptor was tested by Electrostatic paper Analyzer Model EPA-8100 manufactured by Kawaguchi Electric, Japan to determine its photoconductivity. The corona charge was set at −5.0 kV and the corona charge speed was set at 5 m/min. The initial surface potential on the sample was recorded as Vo. After 10 seconds of dark decay, the surface potential was recorded as $V_{10}$. The sample was then exposed under a tungsten light source of 5 Lux intensity and the surface potential began to attenuate. The light energy consumed until the surface potential dropped to a half of $V_{10}$ (half decay exposure) was calculated and recorded as $E_{\frac{1}{2}}$ (in Lux.sec). The surface potential after tungsten exposure was recorded as $V_R$. The following results were obtained:

$V_o = 850$ Volt  $E_{\frac{1}{2}} = 1.5$ Lux.sec  $V_R = 10$ Volt

EXAMPLE 2

The procedure and conditions of Example 1 were followed, but the hydrazone compound was replaced by the hydrazone compound of the formula

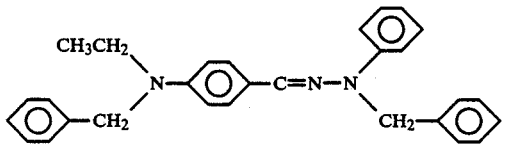

The results were:

$C_o$=1060 Volt $E_{\frac{1}{2}}$=1.0 Lux.sec $V_R$=0 Volt

After 400 times of repeated tests, the following results were obtained:

$V_o$=970 Volt $E_{\frac{1}{2}}$=1.0 Lux.sec $V_R$=0 Volt

EXAMPLE 3

The procedure and conditions of Example 1 were followed, but the hydrazone compound was replaced by the hydrazone compound of the formula:

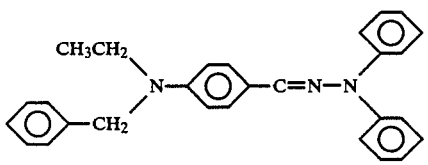

and tetrahydrofuran was used as the solvent instead of toluene.
The results were:

$V_o$=920 Volt $E_{\frac{1}{2}}$=1.0 Lux.sec $V_R$=0 Volt

EXAMPLE 4

The procedure and conditions of Example 2 were followed, but chlorodiane blue was used as the charge generation material instead of copper phthalocyanine and hydroxy squaraine.
The results were:

$V_o$=935 Volt $E_{\frac{1}{2}}$=6 Lux.sec $V_R$=5 Volt

EXAMPLE 5

The procedure and conditions of Example 4 were followed, but the aluminium chloride phthalocyanine (AlClPc) was used as the charge generation material instead chlorodiane blue.
The results were:

Vhd o=990 Volt $E_{\frac{1}{2}}$=3.0 Lux.sec $V_R$=0 Volt

EXAMPLE 6

The procedure and conditions of Example 4 were followed, but the compound of the formula:

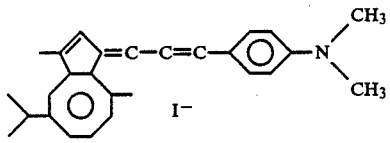

was used as the charge generation material instead of chlorodiane blue.
The results were:

$V_o$=1000 Volt $E_{\frac{1}{2}}$=1.5 Lux.sec $V_R$=15 Volt

EXAMPLE 7

The procedure and conditions of Example 4 were followed, but the charge generation layer coating was replaced by a solution of 0.25 g of hydroxy squaraine, 0.25 g of polyvinyl butyral (BM2 available from Sekisui Co. Japan) and 49.5 g dimethylformamide (DMF).
The results were:

$V_o$=1090 Volt $E_{\frac{1}{2}}$=1.5 Lux.sec $V_R$=15 Volt

EXAMPLE 8

The procedure and conditions of Example 7 were followed, but the charge transport material was replaced by the compound of the formula:

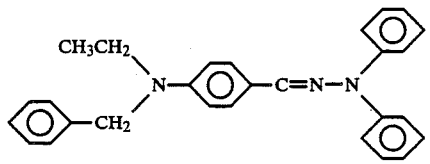

The results were:

$V_o$=880 Volt $E_{\frac{1}{2}}$=2.0 Lux.sec $V_R$=4 Volt

EXAMPLE 9

The procedure and conditions of Example 7 were followed, but the charge transport material was replaced by the compound of the formula:

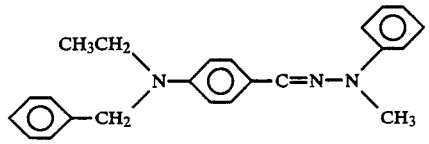

The results were:

$V_o$=960 Volt $E_{\frac{1}{2}}$=2.5 Lux.sec $V_R$=20 Volt

COMPARATIVE EXAMPLE 1

The same procedure and conditions of Example 7 were followed using hydroxy squaraine as the charge generation material, but the charge transport layer coating was replaced by a solution containing 0.4 g of a compound of the formula:

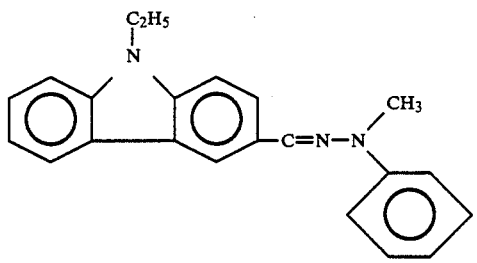

0.5 g of polycarbonate (K1300 available from Teijin Co., Japan), 1.75 g of 1,2-dichloro ethane and 1.75 g of dichloro methane.
The results were:

$V_o$=730 Volt $E_{\frac{1}{2}}$=5 Lux.sec $V_r$=100 Volt

COMPARATIVE EXAMPLE 2

The same procedure and conditions of Comparative Example 1 were followed but the charge transport material was replace by a compound of the formula:

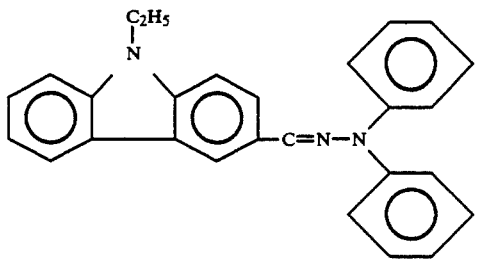

The results were:

$V_o = 810$ Volt  $E_{\frac{1}{2}} = 6.3$ Lux.sec  $V_R = 160$ Volt

COMPARATIVE EXAMPLE 3

The same procedure and conditions of Comparative Example 1 were followed but the charge transport material was replace by a compound of the formula:

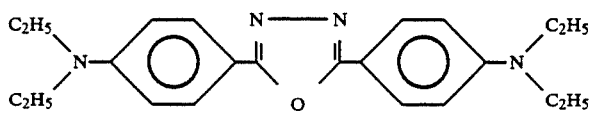

The results were:

$V_o = 790$ Volt  $E_{\frac{1}{2}} = 15$ Lux.sec  $V_R = 220$ Volt

COMPARATIVE EXAMPLE 4

The same procedure and conditions of Comparative Example 1 were followed but the charge transport material was replace by a compound of the formula:

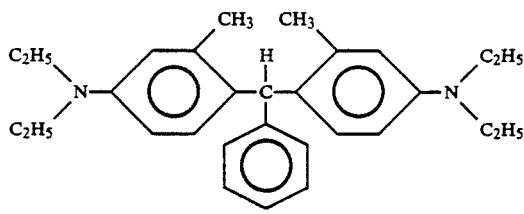

the polymeric binder for the charge transport material was replaced by polymethyl methacrylate (BR80 available from Mitsubishi Rayon Co., Japan), and the solvent was replaced by tetrahydrofuran.

The results were:

$V_o = 1025$ Volt  $E_{\frac{1}{2}} = 27.5$ Lux.sec  $V_R = 319$ Volt

As shown by the above examples, the hydrazone compounds when used as the charge transport material can function well with different charge generation materials to realize electrophotoreceptors of high sensitivity and residual surface potential while prior charge transport materials cannot. The photoreceptor according to the present invention exhibits low residual potential even after repeated uses and thus is highly durable for practical usage.

While only limited embodiments of the present invention have been shown and described herein, it will be appreciated that modifications thereof, some of which have been alluded to hereinabove, may still be readily made thereto by those skilled in the art. We, therefore, intend by the appended claims to cover the modifications alluded to herein as well as all other modifications which fall within the true spirit and scope of our invention.

I claim:

1. An electrophotoreceptor comprising the components of:
   an electrically conductive substrate; a charge generation layer comprising a charge generation material capable of generating electron-hole pair upon exposure under a selected light; and
   a charge transport layer comprising a polymeric binder and a hydrazone compound of formula (I)

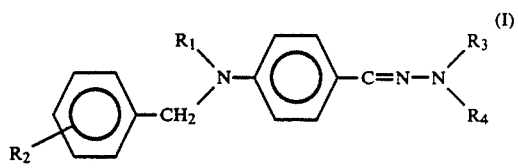

in which $R^1$ represents substituted or unsubstituted $C_1$–$C_4$ alkyl, $R_2$ represents hydrogen, alkyl or alkoxy, $R_3$ and $R_4$ and independently represent substituted or unsubstituted alkyl group substituted or unsubstituted aryl group or substituted or Unsubstituted aralkyl group, or together with the bonded nitrogen atom represent substituted or unsubstituted aromatic heterocyclic ring.

2. The electrophotoreceptor according to claim 1, wherein at least one of $R_3$ and $R_4$ is an aryl group.

3. The electrophotoreceptor according to claim 1, wherein $R_1$ represents ethyl and $R_2$ represents hydrogen.

4. The electrophotoreceptor according to claim 1, wherein said hydrazone compound is selected from the group consisting of compounds of the formulae:

1
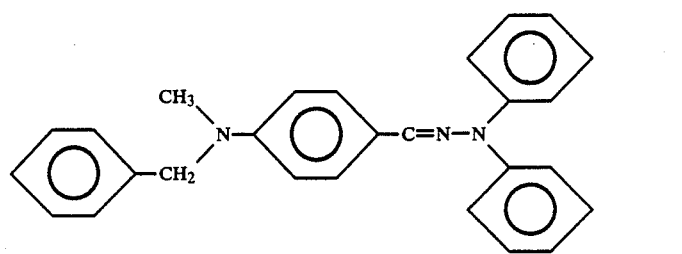
2
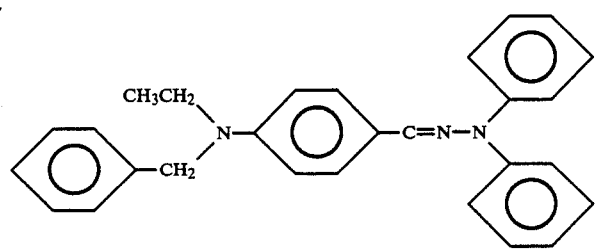
3
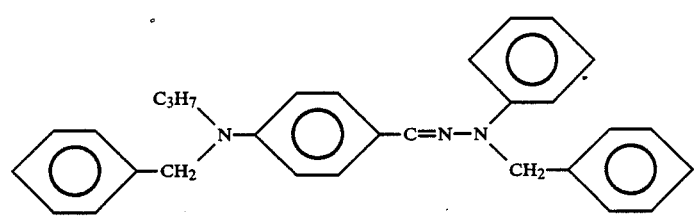
4
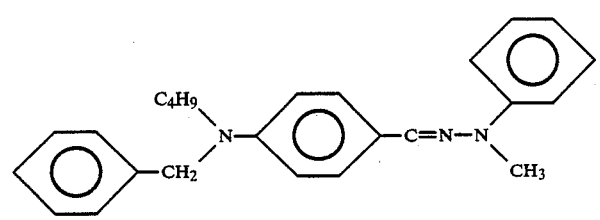
5
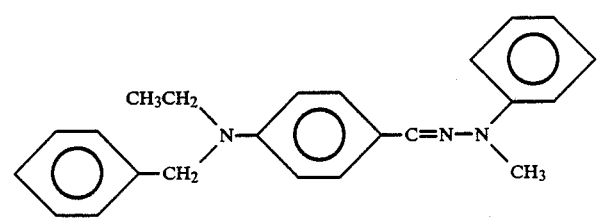
6
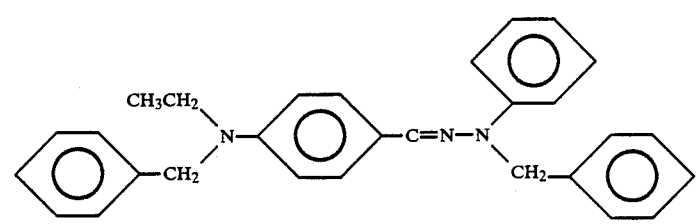

-continued
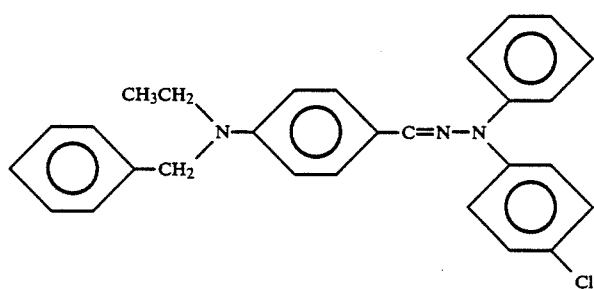
7
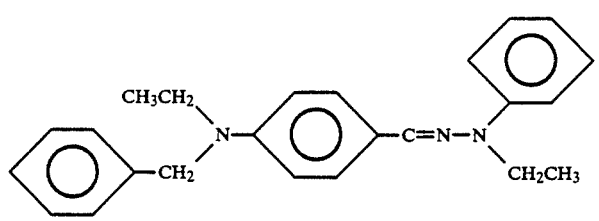
8
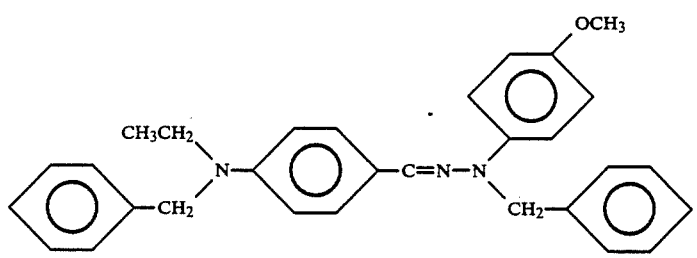
9
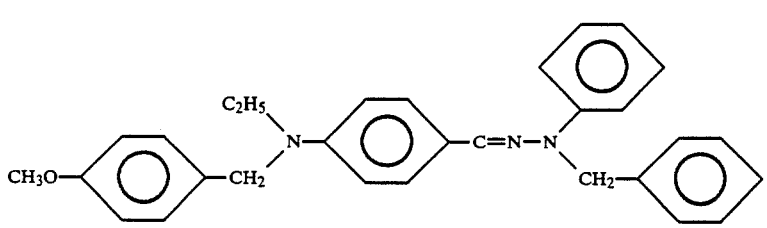
10
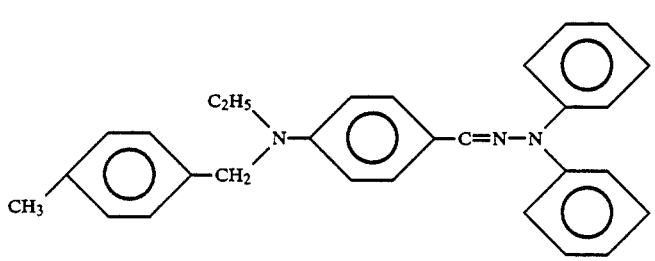
11
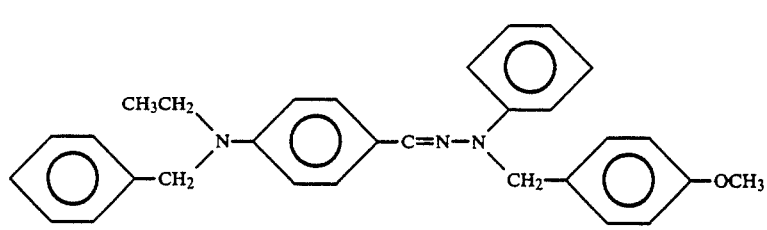
12

-continued
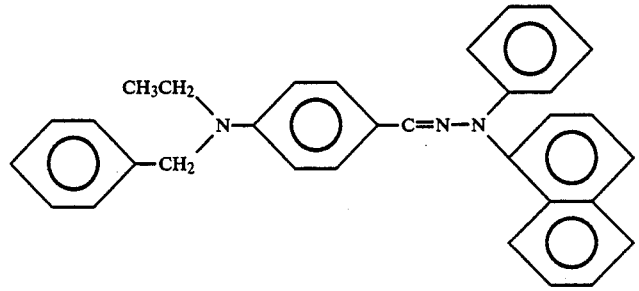
13
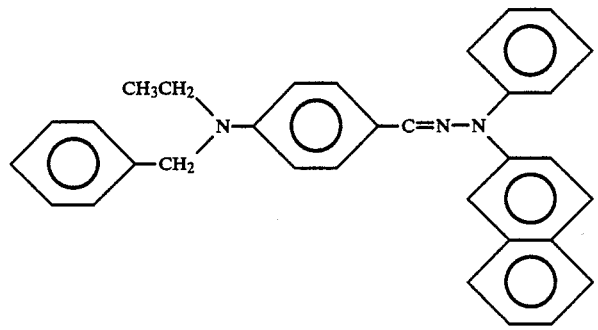
14
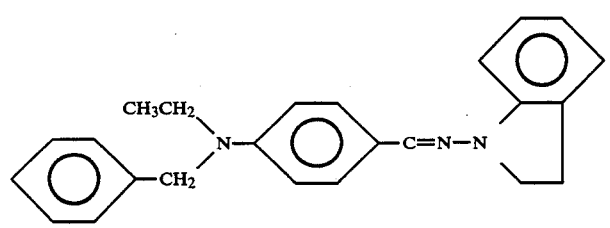
15
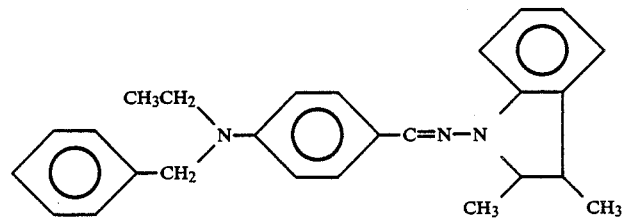
16
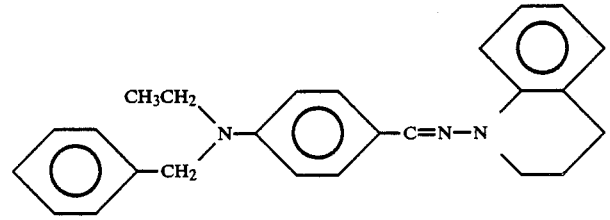
17
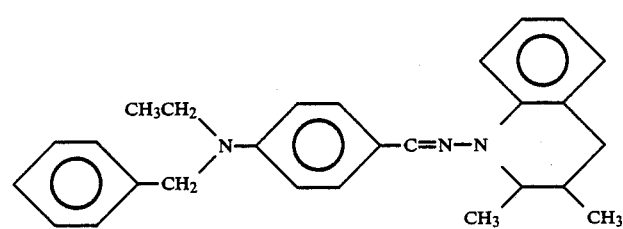
18

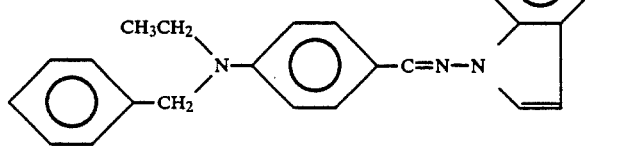
19
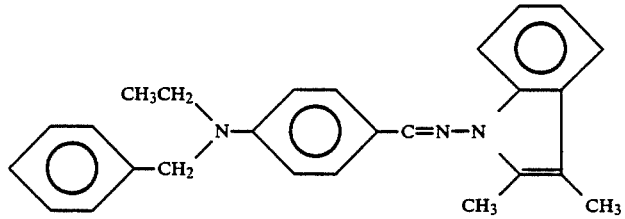
20
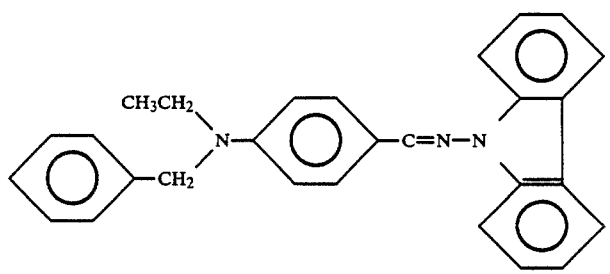
21
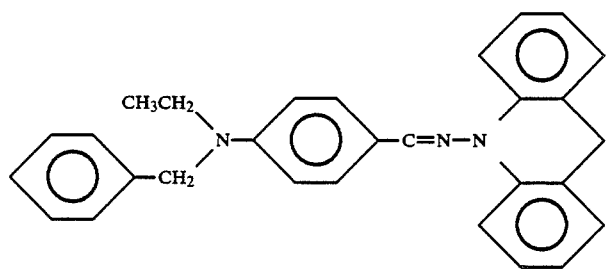
22
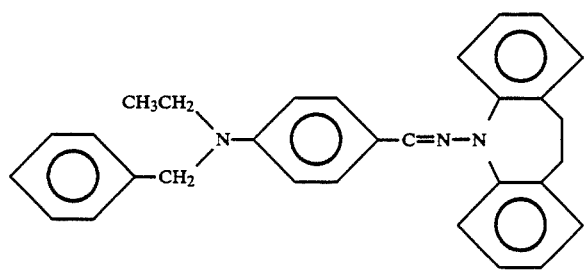
23
5. The electrophotoreceptor according to claim 1, wherein said hydrazone compound is selected from the group consisting of compounds of the formulae:

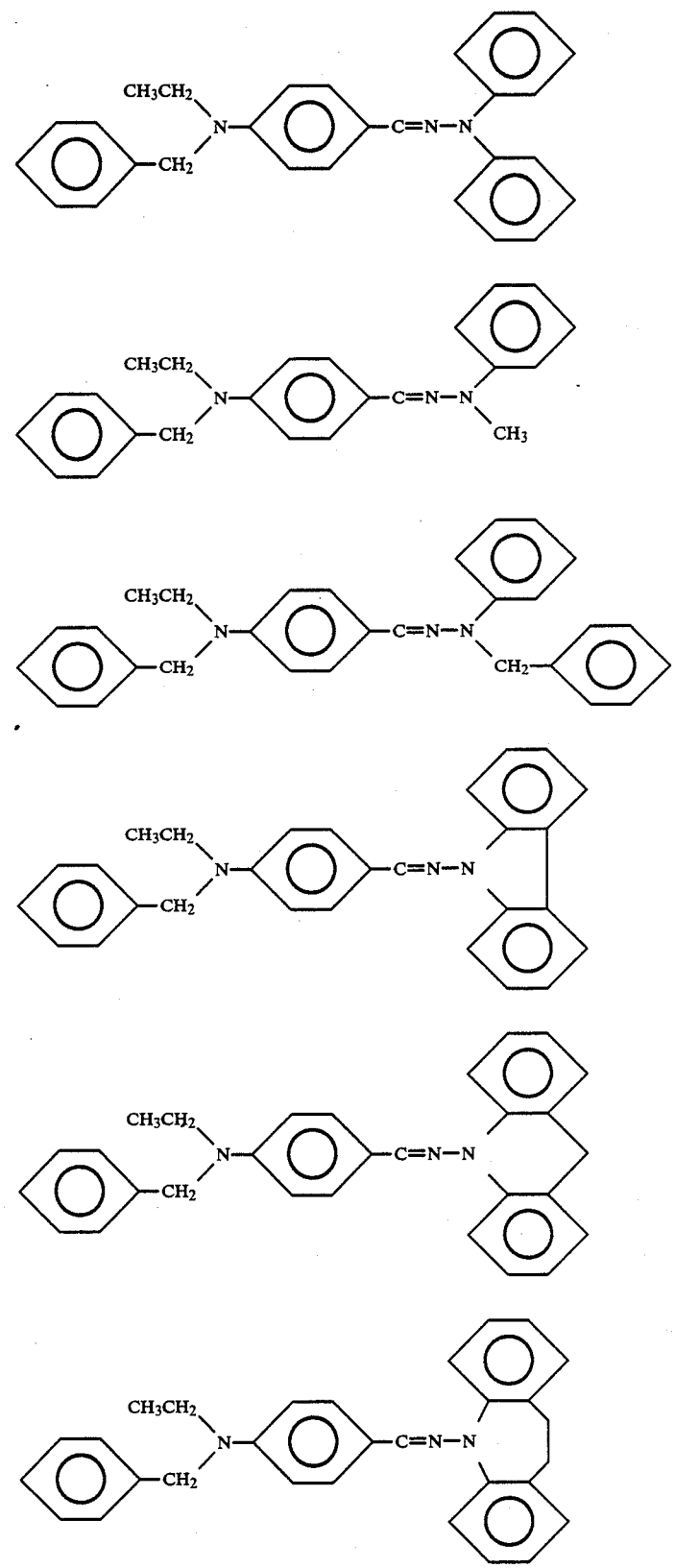
6. The electrophotoreceptor according to claim 1, wherein said hydrazone compound is selected from the group consisting of compounds of the formulae:

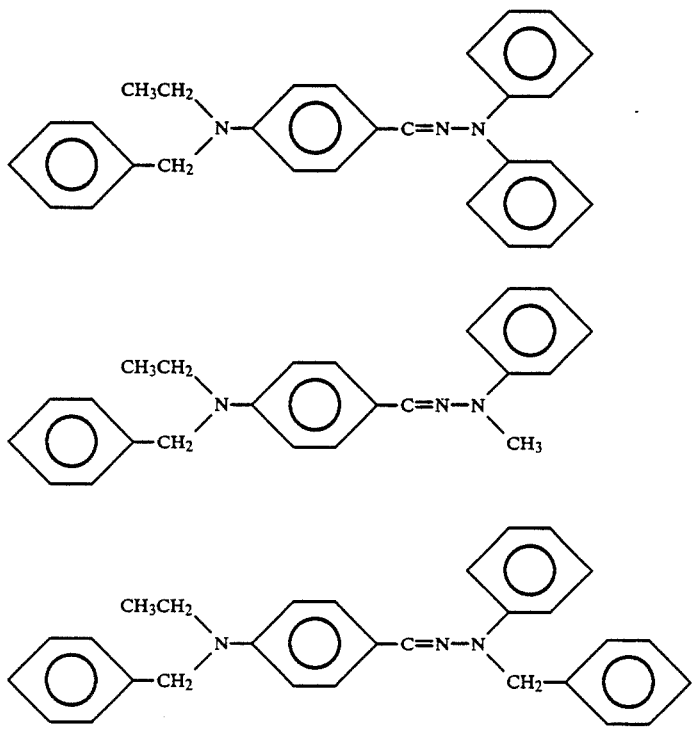

7. The electrophotoreceptor according to claim 1, wherein said charge generation layer is interposed between said substrate and said charge transport layer.

8. The electrophotoreceptor according to claim 1, wherein the thickness of said charge generation layer is between 0.01 g/m² and 5 g/m².

9. The electrophotoreceptor according to claim 7, wherein the thickness of said charge generation layer is between 0.04 g/m² and 2 g/m².

10. The electrophotoreceptor according to claim 1, wherein the thickness of said charge transport layer is between 3 um and 50 um.

11. The electrophotoreceptor according to claim 9, wherein the thickness of said charge transport layer is between 10 um and 25 um.

12. The electrophotoreceptor according to claim 1, wherein said charge generation material is selected from the group consisting of selenium, selenium-tellurium alloy, selenium-arsenic alloy, cadmium, sulfide, phthalocyanine pigment, perinone pigment, thioindigo pigment, quinacridone pigment, perylene pigment, anthraquinone pigment azo pigment, bisazo pigment, cyanine pigment and squaraine pigment.

13. The electrophotoreceptor according to claim ii, wherein said charge generation material is a mixture pigment of phthalocyanine and squaraine.

* * * * *

UNITED STATES PATENT AND TRADEMARK OFFICE
CERTIFICATE OF CORRECTION

PATENT NO. : 4,957,836

DATED : September 18, 1990

INVENTOR(S) : Tai-Jun Chen

It is certified that error appears in the above-identified patent and that said Letters Patent is hereby corrected as shown below:

On the Title page, No. 57, in the abstract, "reproductibility" should read as --reproducibility--.

Column 1, Line 33, "a" should read as --as--.

Column 1, Line 42, delete "n" after "in".

Column 2, Line 45, "Or" should read as --or--.

Column 11, Line 9, "anthraquine" should read as --anthraquinone--.

Column 11, Line 21, "4-chlkoro" should read as --4-chloro--.

Column 12, Line 7, "0.068 of" should read as --0.068 g of--.

Column 12, Line 21, "bulanone" should read as --butanone--.

Column 12, Line 21, "mlcronizing mill" should read as --micronizing mill (--.

Column 12, Line 45, "paper" should read as --Paper--.

Column 13, Line 11, "$C_o$" should read as --$V_o$--.

Column 13, Line 51, "Vhd o" should read as --$V_o$--.

Column 14, Line 68, "$V_r$" should read as --$V_R$--.

Column 15, Line 68, "319" should read as --318--.

UNITED STATES PATENT AND TRADEMARK OFFICE
CERTIFICATE OF CORRECTION

PATENT NO. : 4,957,836

DATED : September 18, 1990

INVENTOR(S) : Tai-Jun Chen

It is certified that error appears in the above-identified patent and that said Letters Patent is hereby corrected as shown below:

Column 16, Line 5, before "residual" insert --low--.

Column 16, Line 55, Claim 1, delete "and" after "$R_4$".

Column 16, Line 57, Claim 1, "Unsubstituted" should read as --unsubstituted--.

Column 28, Line 42, Claim 13, "ii" should read as --11--.

Signed and Sealed this

Twenty-first Day of January, 1992

Attest:

HARRY F. MANBECK, JR.

*Attesting Officer*     *Commissioner of Patents and Trademarks*